United States Patent
Mainville

(10) Patent No.: US 7,855,196 B2
(45) Date of Patent: Dec. 21, 2010

(54) COMPOSITION COMPRISING A BENZODIAZEPINE AGONIST AND A BENZODIAZEPINE ANTAGONIST

(75) Inventor: Pierre Mainville, 295 Chutes Wilson, Saint-Jerome, Quebec (CA) J7Y 4Z7

(73) Assignee: Pierre Mainville (CA)

( * ) Notice: Subject to any disclaimer, the term of this patent is extended or adjusted under 35 U.S.C. 154(b) by 1380 days.

(21) Appl. No.: 11/208,506

(22) Filed: Aug. 22, 2005

(65) Prior Publication Data

US 2007/0043032 A1 Feb. 22, 2007

(51) Int. Cl.
*A01N 43/62* (2006.01)
*A01N 43/42* (2006.01)
*A61K 31/44* (2006.01)

(52) U.S. Cl. .................. 514/219; 514/221; 514/284

(58) Field of Classification Search ............ 514/219, 514/221, 284
See application file for complete search history.

(56) References Cited

U.S. PATENT DOCUMENTS

| | | | |
|---|---|---|---|
| 4,508,726 A * | 4/1985 | Coleman | 514/220 |
| 4,595,684 A | 6/1986 | Bennett | 514/221 |
| 4,666,903 A | 5/1987 | Gallager | 514/220 |
| 4,713,383 A | 12/1987 | Francis et al. | 514/267 |
| 4,925,844 A | 5/1990 | Resch | 514/252 |
| 6,534,500 B2 | 3/2003 | D'Alche-Biree | 514/226.2 |
| 6,593,094 B2 * | 7/2003 | Lanzara | 435/7.21 |
| 2006/0167068 A1 * | 7/2006 | Feuerstein et al. | 514/367 |

FOREIGN PATENT DOCUMENTS

| | | | |
|---|---|---|---|
| CA | 2436511 | 2/2002 | ............... 25/30 |
| WO | WO 99/63933 | 12/1999 | |

OTHER PUBLICATIONS

Moy et al. Psychopharmacology, 2000, vol. 152, pp. 208-215.*
Fernandez, F. et al., Analgesic effect of alprazolam in patients with chronic, organic pain of malignant origin, 1987, J. of Clinical Psychopharmacology, 7: 167-169 Farrar, J. et al., Clinical importance of changes in chronic pain intensity measured on an 11-point numerical pain rating scale, 2001, Pain 94:149-158.
Sosnowski, M. and T.L. Yaksh, Spinal administration of receptor-selective drugs as analgesics: New Horizons. J. Pain Symptom.Manage.5: 204-213, 1999.

* cited by examiner

*Primary Examiner*—Sreeni Padmanabhan
*Assistant Examiner*—Samira Jean-Louis
(74) *Attorney, Agent, or Firm*—Byron A. Bilicki, Esq.; The Bilicki Law Firm, PC

(57) ABSTRACT

A composition comprising a benzodiazepine agonist, a benzodiazepine antagonist, and a pharmaceutical acceptable carrier in an effective ratio so as to preserve the therapeutic effects of the benzodiazepine agonist while modulating the side effects of the benzodiazepine agonist.

4 Claims, No Drawings

COMPOSITION COMPRISING A BENZODIAZEPINE AGONIST AND A BENZODIAZEPINE ANTAGONIST

FIELD OF THE INVENTION

The invention relates to a composition comprising a benzodiazepine agonist and a benzodiazepine antagonist.

BACKGROUND

Gamma-amino butyric acid (GABA) is considered one of the major inhibitory neurotransmitter in the central nervous system (Sosnowski, M. and T. L. Yaksh, 1990, Spinal administration of receptor-selective drugs as analgesics: New Horizons. J. Pain Symptom. Manage. 5: 204-213). When released, GABA interacts with receptors present on the cell membrane which results in a reduction of neuronal excitability. GABA receptors can be divided in three classes, $GABA_A$, $GABA_B$ and $GABA_C$.

$GABA_A$ receptors belong to the superfamily of ligand-gated chloride ion channel receptors and constitute the site of action of many drugs. Accordingly, the binding of GABA to its receptor can be modulated by simultaneous binding of different chemical entities to allosteric sites on the ion channel complex. One of these allosteric sites is the benzodiazepine binding site. Ligands of the benzodiazepine binding site on the $GABA_A$ receptor complex are either agonists, antagonists or inverse agonists.

Benzodiazepines, widely used for their antidepressant, anxiolytic, sedative, myorelaxant, and anticonvulsant properties, modulate the binding of GABA to $GABA_A$ receptors. Benzodiazepines have also been reported in the treatment of chronic pain (Fernandez F. et al., 1987, Analgesic Effect of Alprazolam in Patients With Chronic, Organic Pain of Malignant Origin, J. of Clinical Psychopharmacology, 7:167-169). For example, benzodiazepine agonists increase the binding of GABA to $GABA_A$ receptor and promote $Cl^-$ influx. Examples of such benzodiazepine agonists include alprazolam (8-chloro-1-methyl-6-phenyl-4H-s-triazolo[4,3-a][1,4] benzodiazepine), bromazepam, chlordiazepoxide, clonazepam, clorazepate dipotassium, diazepam, estazolam, flurazepam, halazepam, lorazepam, midazolam, nitrazepam, oxazepam, quazepam, temazepam and triazolam.

The long-term high-dose use of benzodiazepines agonists can be problematic due to the decrease in the efficacy of the $GABA_A$ receptors leading to the development of tolerance and dependence. The principal side effects of the benzodiazepines are sedation, paradoxal effects, sleepiness, fatigue, weakness, cognitive and/or motor impairment. Moreover, cessation of benzodiazepines may produce withdrawal symptoms with resultant anxiety, insomnia, reduced appetite and weight, perceptual disturbances and tremor.

Several ligands can block the actions of benzodiazepine agonists by competitive inhibition of benzodiazepine receptors. Benzodiazepine antagonists are used, for example, to reverse the adverse pharmacological effects of benzodiazepine agonists, such as their sedative effects, to regenerate the sensitivity response and prevent tolerance of benzodiazepine and for the management of benzodiazepine overdose. Such uses are well known in the art and are described, for example, in U.S. Pat. Nos. 4,595,684, 4,666,903, 4,713,838 and 4,925,844.

SUMMARY OF THE INVENTION

The invention relates to a composition comprising a benzodiazepine agonist, a benzodiazepine antagonist, and a pharmaceutical acceptable carrier in an effective ratio so as to preserve the therapeutic effects of the benzodiazepine agonist while modulating the side effects of the benzodiazepine agonist.

The invention also relates to the use of a benzodiazepine agonist and a benzodiazepine antagonist in an effective ratio so as to preserve the therapeutic effects of the benzodiazepine agonist while modulating the side effects of the benzodiazepine agonist.

DETAILED DESCRIPTION OF EMBODIMENTS OF THE INVENTION

The present invention provides a composition comprising a benzodiazepine agonist and a benzodiazepine antagonist in an appropriate ratio to prevent tolerance, side effects and withdrawal symptoms by the patient while preserving the therapeutic benefits of the benzodiazepine agonist and allowing an higher dosage of the latter.

One embodiment of the composition of the present invention is useful in the treatment of chronic and neuropathic pain. It is also useful in the treatment of anxiety, depression, pain associated with post-traumatic stress disorder, epilepsy, fibromyalgia, arterial hypertension, dysautonomia, endotoxic and anaphylactic shock, tinnitus, neurodegenerative and neuroinflammatory diseases, immunomodulator dysfunctions, alcohol poisoning, and obesity.

The benzodiazepine agonists used according to the present invention include alprazolam, bromazepam, chlordiazepoxide, clonazepam, clorazepate dipotassium, diazepam, estazolam, flurazepam, halazepam, lorazepam, midazolam, nitrazepam, oxazepam, quazepam, temazepam and triazolam. Preferred benzodiazepine agonists are alprazolam, chlordiazepoxide, clonazepam, diazepam, lorazepam, midazolam, oxazepam, temazepam, and triazolam.

The benzodiazepine antagonists used include flumazenil, NPI-031G (puerarin), ethyl 5-isopropoxy-4-methyl-beta-carboline-3-carboxylate, PK 11195, Ro15-3505, ZK93,426, CGS 9896, RO14-7437, CGS8216, 3-HMC, U89843A. PK1195, FG 7142, (+)-bicuculline, (−)-bicuculline methobromide, (−)-bicuculline methochloride, picrotoxin, and SR 95531. One example of benzodiazepine antagonist is flumazenil.

These compounds are well known in the art and will not be described in further detail in the written description.

The agonists and antagonists may be formulated for oral, parenteral, nasal, sub-lingual, rectal or olphthalmic use. The term parenteral as used herein includes subcutaneous injections, intravenous, intramuscular, intrasternal injection or infusion techniques.

The agonists and antagonists may be in the form of tablets or capsules prepared by conventional means with pharmaceutically acceptable excipients such as binding agents (e.g. carboxymethylcellulose, pregelatinised starch); fillers (e.g. lactose, microcrystalline cellulose); lubricants (e.g. magnesium stearate, talc); disintegrants (e.g. potato starch or sodium starch glycolate); or wetting agents (e.g. sodium lauryl sulphate). The tablets may be coated by methods well known in the art. Liquid preparations for oral administration may take the forms of solutions, suspensions, or syrups and may be presented as a dry product for constitution with water or other suitable vehicle before use. Such liquid preparations may be prepared by conventional means with pharamaceutivcally acceptable additives such as suspending agents (e.g. sorbitol syrup); emulsifying agents (e.g. lecithin); non-aqueous vehicles (e.g. oily esters, oils, ethyl alcohol); and preservatives (e.g. hydroxybenzoates or sorbic acid).

The compounds of the invention may be formulated for parenteral administration by bolus injection. Formulations for injection may be presented in unit dosage form, e.g. in ampoules or in multi-dose containers, with an added preservative. The compositions may be in the form of suspensions, solutions, or emulsions in oily or aqueous vehicles, and may contain suspending, stabilizing, and/or dispersing agents. Alternatively, the active ingredient may be in powder form for constitution with a suitable vehicle before use.

In one embodiment, the pharmaceutical composition is administered to a human patient 1 to 4 times a day or by a controlled release formulation. The term "controlled release" as used herein means any formulation technique wherein release of the antagonist is modified to occur at a slower rate than that of the agonist. Such formulations are prepared by conventional means.

The agonists and antagonists may be administered to a patient simultaneously or sequentially.

The techniques for the preparation of these pharmaceutical compositions are well known in the art and reference may be had to Remington's Pharmaceutical Sciences, 18th Edition, Mack Publishing Co. Easton, Pa., U.S.A. 18042.

The benzodiazepine agonist and the benzodiazepine antagonist are generally present in a weight ratio from about 1:1 to about 200:1. In specific embodiments, the ratio is from about 5:1 to about 100:1. In one exemplary embodiment, the pharmaceutical composition comprises alprazolam and flumazenil in a weight ratio from about 1:1 to about 200:1 In an alternate embodiment, the ratio is from about 5:1 to about 100:1. The use of the benzodiazepine agonist and antagonist in these specified ratios prevents tolerance, side effects, and withdrawal symptoms by the recipient while preserving the therapeutic benefits of the benzodiazepine agonist. Moreover, it allows for the use of higher benzodiazepine agonist dosages.

The specific ratio for a patient will depend from a variety of factors including the compounds employed, the age, body weight, health, sex, route of administration, drug combination, disease, and other factors well known by a person skilled in the art.

In the following examples, the patient's baseline of pain was monitored using the 11-point numerical pain rating scale of Farrar et al. (Farrar, J. and James P. Young Jr. 2001, Pain 94(2): 149-158). In accordance with this scale, the patient rates his or her pain on a scale of 1 to 10. As determined by Farrar et al., any improvement resulting in a decrease in the perception of pain by 30%, is 76.51 sensitive and 80.09 specific.

The following examples are provided to illustrate the invention. They are not in any way intended to limit the scope of the invention in any manner or to any degree.

EXAMPLE 1

The use of Alprazolam in the Treatment of Neuropathic Pain

This example serves as a control as no antagonist was used. It serves to illustrate the limitations of a therapy consisting only of a benzodiazepine agonist, in view of the sedative effects on the patient. A 58-year-old male suffering from a progressive perineal neuropathic pain refractory to strong narcotics, synthetic THC, antidepressant and antiepileptic was treated with 0.5 mg of alprazolam three times a day (TID) and 2 mg of alprazolam at bedtime (HS). The patient noticed an increased period of pain remission. However, an augmentation of the dosage of alprazolam was impossible due to severe patient sedation.

EXAMPLE 2

The use of Midazolam and Alprazolam in the Treatment of Phantom Pain.

This example also serves as a control. Two different types of agonists are used to treat the pain. Again, the beneficial effects of the therapy are limited in view of the sedative effects of the agonists. A 30-year-old male suffering from phantom pain, after amputation of both arms, partially responding to 800 mg gabapentin four times a day (QID) and fentanyl patches 125 µg/hour, was treated with 2 mg of midazolam iv. His pain level improved from $7/10$ to $0/10$. However, the patient experienced sedation. Then, 0.25 mg of alprazolam QID was administered with sustained results. An augmentation of the dosage of alprazolam was impossible due to severe sedation.

EXAMPLE 3

The use of Alprazolam and Flumazenil in the Treatment of Phantom-Like Pain

A 43-year-old anxious paraplegic male with phantom-like pain of both legs after a severe spinal trauma was treated with 6 mg a day of alprazolam. Then, 100 µg of flumazenil was administered to the patient, and, 5 minutes after injection, the patient's low back pain diminished from $7/10$ to $5/10$. This example also points to a synergy between the benzodiazepine agonist and antagonist.

EXAMPLE 4

The use of Midazolam and Flumazenil in the Treatment of Causalgia

A 50-year-old male suffering from a right arm complex regional pain syndrome type 2 (formerly causalgia) rated his pain at $5/10$. The patient was treated with 2 mg of midazolam iv. After 5 minutes, the patient rated his pain to $3/10$ (40% improvement). The sedative effects of the agonist were reversed 5 minutes after the administration of midazolam with 200 µg of flumazenil iv (ratio 10:1) without altering the midazolam response to pain.

EXAMPLE 5

The use of Midazolam and Flumazenil in the Treatment of Reflex Sympathetic Dystrophy A 67-year-old male suffering from a left knee complex regional pain syndrome (CRPS) type 1 (formerly reflex sympathetic dystrophy) after total knee replacement was treated with 2 mg of midazolam iv. The level of pain was lowered from $8/10$ to $3/10$ and the patient did not present any signs of sedation. Then, the patient received 200 µg of flumazenil iv and his pain disappeared. This example demonstrates again a synergy between the benzodiazepine agonist and antagonist.

EXAMPLE 6

The use of Midazolam and Flumazenil in the Treatment of Reflex Sympathetic Dystrophy A 31-year-old female suffering from a reflex sympathetic dystrophy type 1 of right upper extremity was treated with 2 mg of midazolam iv, and, after 5 minutes, her pain level was lowered from 4/10 to 0/10. However, moving her arm increased the pain to 4-5/10. Then, 200 μg of flumazenil iv was administered and her pain level diminished to 1/10 while she was moving her arm. The experience was repeated one hour later and the same phenomenon was observed. Once again, this example demonstrates a synergy between the benzodiazepine agonist and antagonist.

EXAMPLE 7

The use of Midazolam and Flumazenil in the Treatment of Reflex Sympathetic Dystrophy A 44-year-old female suffering from a chronic reflex sympathetic dystrophy type 1 of her right knee with severe anxiety was treated simultaneously with 5 mg of midazolam iv and 500 μg of flumazenil iv. At this point, she rated her pain at 5/10. Less than 15 minutes after treatment, her pain went down to 0/10 without any sedative effects.

EXAMPLE 8

The use of Alprazolam, Midazolam and Flumazenil in the Treatment of Chronic Post-Traumatic Pain A 32-year-old male suffering from a chronic post-traumatic central pain refractory to narcotics, tricyclic antidepressant, and antiepileptic was treated with 5 mg/day of alprazolam. While his pain rating improved from 6/10 to 4/10, he experienced alprazolam side effects. 5 mg of midazolam and 500 μg of flumazenil iv were administered simultaneously to the patient. After 15 minutes, the pain diminished from 8/10 to 5/10. Ten minutes later, the patient was treated with 300 μg of flumazenil iv, and, after 5 minutes, he rated his pain at 3/10 with minimum sedative effect. Finally, 25 minutes after treatment, his pain was of the order of 4/10. This example illustrates once more a synergy between the benzodiazepine agonist and antagonist.

EXAMPLE 9

The use of Midazolam and Flumazenil in the Treatment of Chronic Fibromyalgia

A 59-year-old female suffering from chronic fibromyalgia was treated simultaneously with 2 mg of midazolam iv and 200 μg of flumazenil iv. At this point, she rated her pain at 7/10. Less than 30 minutes after treatment, her pain went down to 0/10 without any sedative effects.

EXAMPLE 10

The use of Midazolam and Flumazenil in the Treatment of Fibromyalgia and Depression A 50-year-old female suffering from chronic severe fibromyalgia and chronic depression was treated simultaneously with 5 mg of midazolam iv and 500 μg of flumazenil iv. At this point, she rated her pain at 5/10. Fifteen minutes after treatment, her pain went down to 3/10 with very low sedative effects. This patient had already received buspirone 20 mg QID, gabapentin 600 mg QID, 150 mg of fluvoxamine once a day, and 0.25 mg of alprazolam TID, and as such, would have been expected after taking midazolam to experience far more sedation than actually experienced.

The above examples illustrate the unexpected advantages of the composition of the present invention which modulates the side effects of the benzodiazepine agonist, particularly sedation, while allowing higher dosages of the agonist. In addition, the examples also point out to a synergistic effect between the agonist and antagonist since use of the antagonist unexpectedly leads in some cases to a further decrease in the pain experienced by the patient, reflecting in all likelihood competitive binding activity at the GABA receptor sites.

While the present invention has been described in connection with specific embodiments thereof and in specific uses, various modifications will occur to those skilled in the art without departing from the spirit and scope of the invention as set forth in the appended claims. While the following claims are intended to recite the features of the invention, it will be apparent to those of skill in the art that certain changes may be made without departing from the scope of this invention.

What is claimed is:

1. A composition comprising a benzodiazepine agonist, a benzodiazepine antagonist, and a pharmaceutical acceptable carrier in an effective ratio so as to preserve the therapeutic effects of the benzodiazepine agonist while modulating the side effects of the benzodiazepine agonist, wherein the benzodiazepine agonist and the benzodiazepine antagonist are in a ratio that provides a synergistic pharmaceutical interaction and wherein the agonist is alprazolam, midazolam, or combinations thereof and the antagonist is fumazenil.

2. The composition of claim 1, wherein the benzodiazepine agonist and the benzodiazepine antagonist are in a weight ratio of 1:1 to 200:1.

3. The composition of claim 1, wherein the benzodiazepine agonist and the benzodiazepine antagonist are in a weight ratio of 5:1 to 100:1.

4. The composition of claim 1, wherein said composition is for the treatment of one or more conditions selected from a group comprised of chronic and neuropathic pain, anxiety, depression, pain associated with post-traumatic stress disorder, epilepsy, fibromyalgia, arterial hypertension, dysautonomia, endotoxic and anaphylactic shock, tinnitus, neurodegenerative and neuroinflammatory diseases, immunomodulator dysfunctions, alcohol poisoning, and obesity.

* * * * *